United States Patent
Flint et al.

(10) Patent No.: US 12,048,638 B2
(45) Date of Patent: Jul. 30, 2024

(54) DUAL-SHAFT IMPLANT EXPANSION DRIVER WITH REVERSIBLE DRIVER KEY MECHANISM AND EXPANDABLE INTER VERTEBRAL IMPLANT SYSTEM

(71) Applicant: GLOBUS MEDICAL, INC., Audubon, PA (US)

(72) Inventors: Brian Flint, Ft. Washington, PA (US); Colm McLaughlin, Glenside, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/465,316

(22) Filed: Sep. 12, 2023

(65) Prior Publication Data

US 2024/0000585 A1  Jan. 4, 2024

Related U.S. Application Data

(63) Continuation of application No. 17/740,961, filed on May 10, 2022, now Pat. No. 11,752,013, which is a continuation of application No. 16/868,747, filed on May 7, 2020, now Pat. No. 11,344,434.

(51) Int. Cl.
*A61F 2/44* (2006.01)
*A61F 2/46* (2006.01)

(52) U.S. Cl.
CPC ............ *A61F 2/4611* (2013.01); *A61F 2/447* (2013.01); *A61F 2/4657* (2013.01); *A61F 2002/4658* (2013.01); *A61F 2002/4668* (2013.01)

(58) Field of Classification Search
CPC .......... A61F 2/44; A61F 2/4611; A61F 2/447; A61F 2/4422; A61F 2/4657; A61F 2002/4658; A61F 2002/4668
USPC ................. 623/17.11–17.16; 606/99–100
See application file for complete search history.

(56) References Cited

U.S. PATENT DOCUMENTS

| | | | |
|---|---|---|---|
| 2009/0024133 A1* | 1/2009 | Keady ............... | A61F 2/966 606/62 |
| 2009/0048604 A1* | 2/2009 | Milz ................. | A61F 2/4603 606/90 |
| 2010/0298834 A1* | 11/2010 | Hildebrandt ....... | A61B 17/1746 606/86 R |
| 2010/0312103 A1* | 12/2010 | Gorek ............... | A61B 17/1703 600/425 |
| 2011/0172716 A1* | 7/2011 | Glerum .............. | A61F 2/4465 606/279 |
| 2014/0316522 A1* | 10/2014 | Weiman ............. | A61F 2/4455 623/17.16 |

(Continued)

*Primary Examiner* — Jessica Weiss

(57) ABSTRACT

A surgical driver apparatus includes a housing and an inner driver shaft having a proximal end secured within the housing and a distal end extending out from a first side of the housing. The inner driver shaft is configured to rotate with respect to the housing. The surgical driver apparatus further includes an outer driver shaft and an idler driver shaft. The outer driver shaft is positioned coaxial with the inner driver shaft and configured to rotate independently from the inner driver shaft. The idler driver shaft is configured to transmit torque to the outer driver shaft. Additionally, the surgical driver apparatus includes a driver key comprising a driving feature and a counter-driving feature. The driver key is configured to engage a second side of the housing in one of a plurality of orientations configured to rotate the inner driver shaft and/or the outer driver shaft.

13 Claims, 16 Drawing Sheets

(56) References Cited

U.S. PATENT DOCUMENTS

2017/0112632 A1* 4/2017 Dmushewsky ....... A61F 2/4611
2019/0231447 A1* 8/2019 Ebbitt .................. A61B 34/30
2019/0350725 A1* 11/2019 Behzadi ............... A61F 2/4657

* cited by examiner

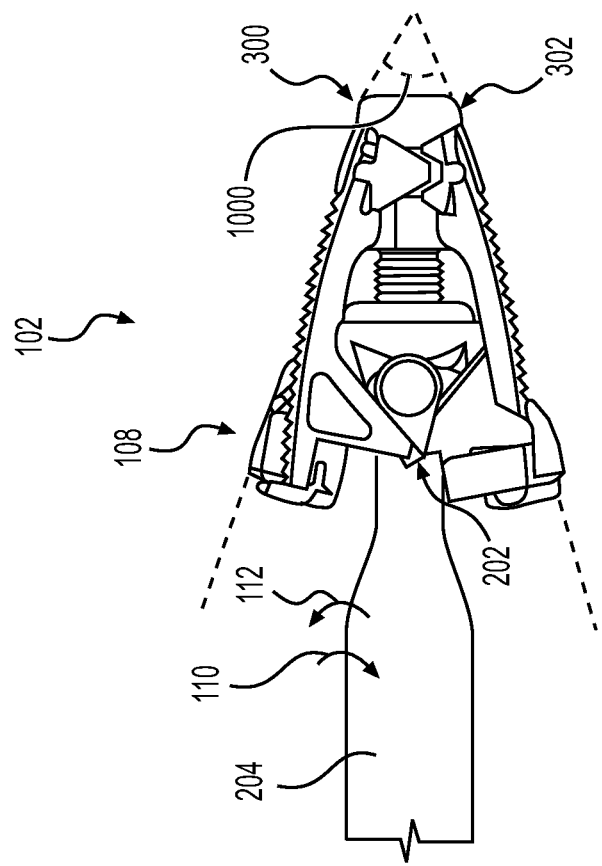
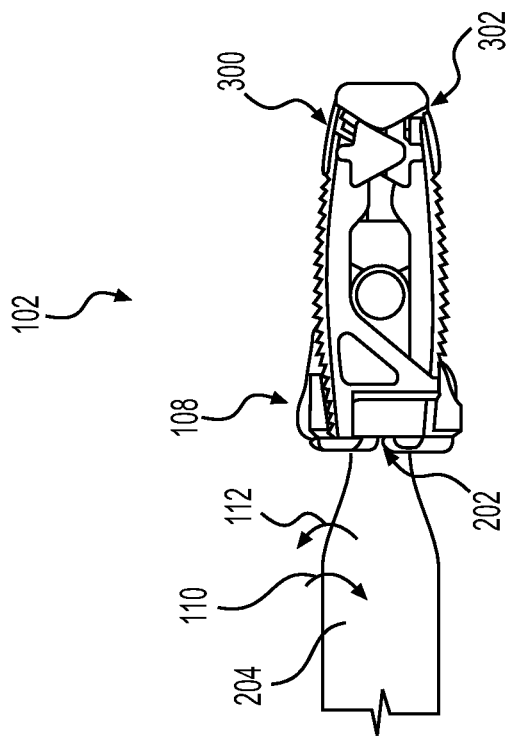
FIG. 10B
FIG. 10A

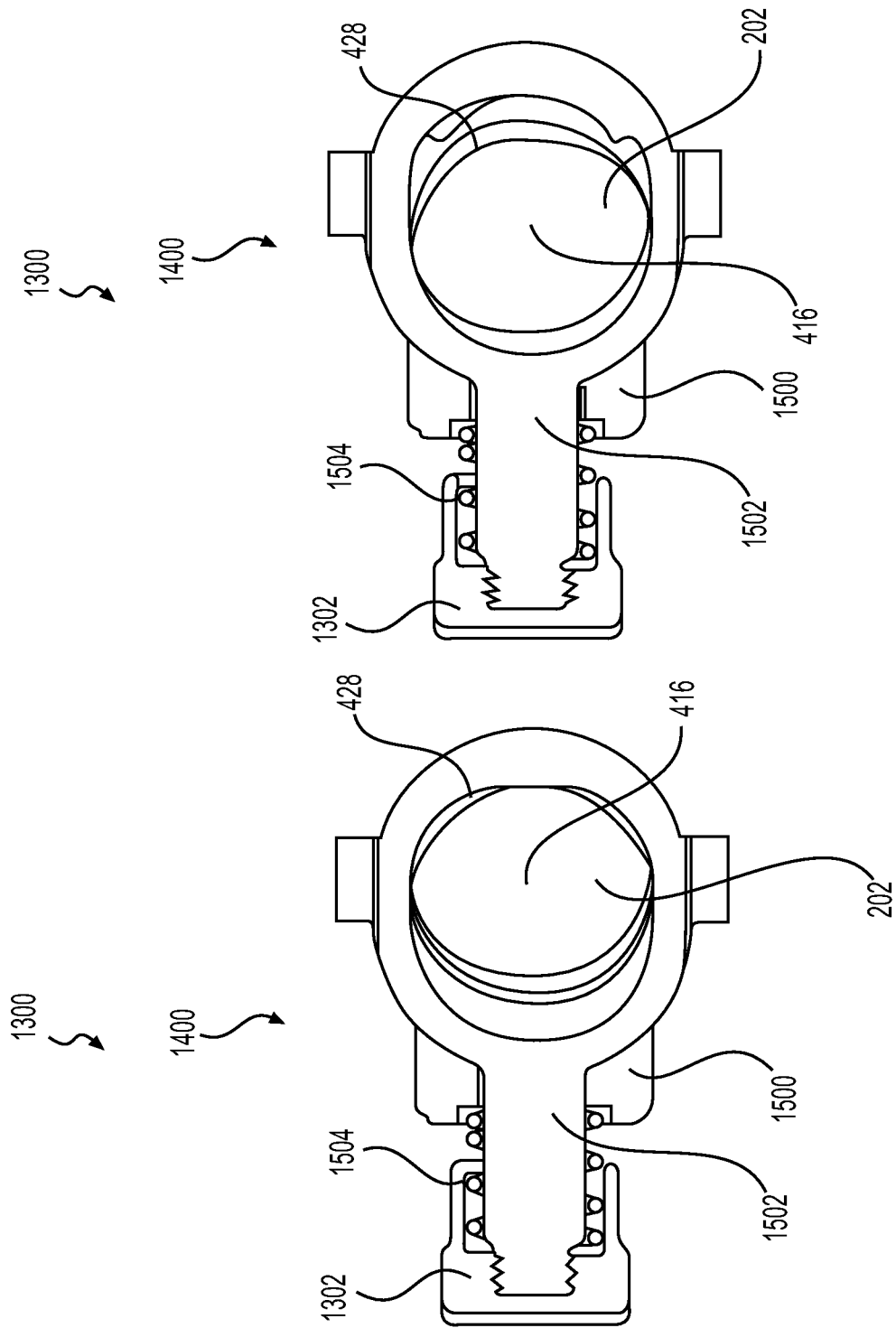

DUAL-SHAFT IMPLANT EXPANSION DRIVER WITH REVERSIBLE DRIVER KEY MECHANISM AND EXPANDABLE INTER VERTEBRAL IMPLANT SYSTEM

CROSS REFERENCE TO RELATED APPLICATIONS

The present application is a continuation of U.S. patent application Ser. No. 17/740,961 filed on May 10, 2022, which is a continuation of U.S. patent application Ser. No. 16/868,747 filed on May 7, 2020 (published as U.S. Pat. Pub. No. 2021-0346174), all of which are incorporated by reference in their entirety herein for all purposes.

BACKGROUND

Intervertebral implants are used for stabilizing adjacent vertebrae of the spine. The implants are inserted between adjacent vertebra of the spine and adjusted based on the condition of the spine. Bones and bony structures (e.g., the spine) are susceptible to a variety of weaknesses that can affect their ability to provide support and structure. Weaknesses in bony structures have numerous potential causes, including degenerative diseases, tumors, fractures, and dislocations. To alleviate or cure these weaknesses, the implant may be adjusted to expand a height or change an angle (e.g., lordotic angle) of the implant. For example, adjusting the angle of the implant may provide additional support at posterior portion of the implant to alleviate weaknesses cause by a curved spine disorder (e.g., lordosis).

Adjusting intervertebral implants requires specialized tools (e.g., drivers). Generally, multiple tools are required or a single tool with separate right-hand and left-hand rotational modes are used to achieve expansion and angulation change of the implant. However, as these tools are used to adjust implants during surgical operations, providing a simpler, more intuitive, and less invasive tool would be advantageous.

BRIEF DESCRIPTION OF THE DRAWINGS

These drawings illustrate certain aspects of some of the embodiments of the present disclosure and should not be used to limit or define the disclosure.

FIGS. 10A and 10B are side views of the implant in a collapsed configuration and an anterior expansion configuration, respectively, according to some embodiments;

FIGS. 16A and 16B are cross-sectional views of a thread follower of the measurement device, according to some embodiments.

DETAILED DESCRIPTION

Figure 1:
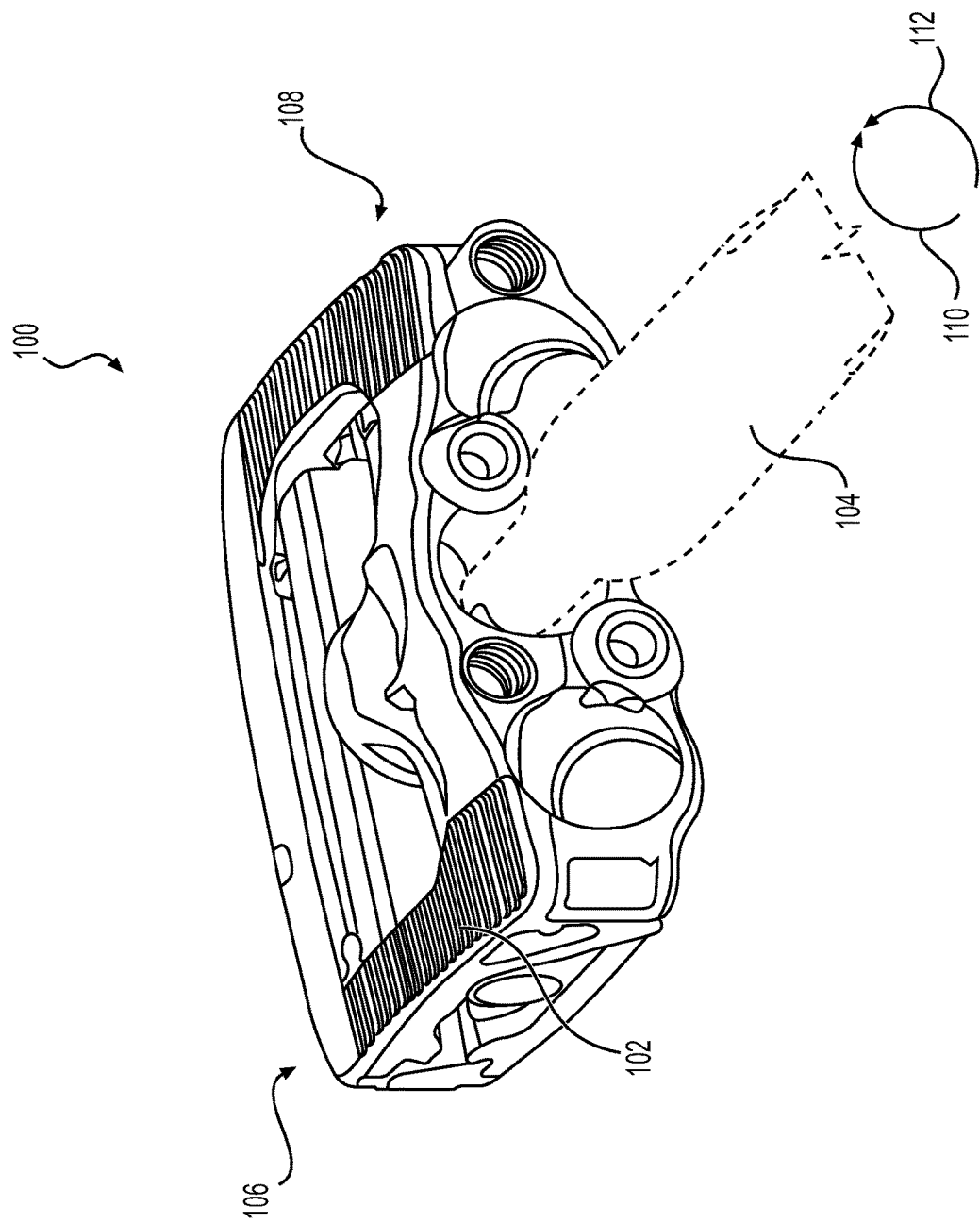
FIG. 1 is a perspective view of a surgical implant system having an implant and a surgical driver, according to some embodiments.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Referring now to the drawings, FIG. 1 illustrates a perspective view of a surgical implant system 100 having an implant 102 (e.g., expandable interbody fusion implant with adjustable angulation) and a surgical driver 104, according to some embodiments. The implant 102 is configured to be inserted between adjacent bones of a joint (e.g., vertebrae) to stabilize the joint. For example, the implant 102 may be inset into intervertebral disc space. To reduce impaction to tissue in the joint space during insertion of the implant 102, the implant 102 may be inserted in a collapsed configuration. After insertion, the surgical driver 104 engages the implant 102 to drive the implant 102 to expand to a desired configuration based at least in part on a condition of the spine. That is, the surgical driver 104 is configured to cause a posterior portion 106 and an anterior portion 108 of the implant 102 to expand individually or simultaneously to the desired configuration for treating a particular condition of the spine.

The implant 102 may achieve various expansion configurations using the surgical driver 104. Further, the surgical driver 104 may provide intuitive operation by causing clockwise rotation 110 of the surgical driver 104 to expand the implant 102 to any suitable expansion configuration in all modes of the surgical driver 104. Similarly, the surgical driver 104 may collapse the implant 102 in all modes of the surgical driver. 104 with counterclockwise rotation 112 of the surgical driver 104, Having, the surgical driver 104 expand the implant 102 with clockwise rotation 110 in all modes and collapse the implant 102 with counterclockwise rotation 112 in all modes may make the surgical implant system 100 intuitive to use, which may minimize the risk of collapsing the implant 102 when expansion is desired and vice-versa. Moreover, the surgical drives 104 includes other advantageous features set forth below.

Figure 2:
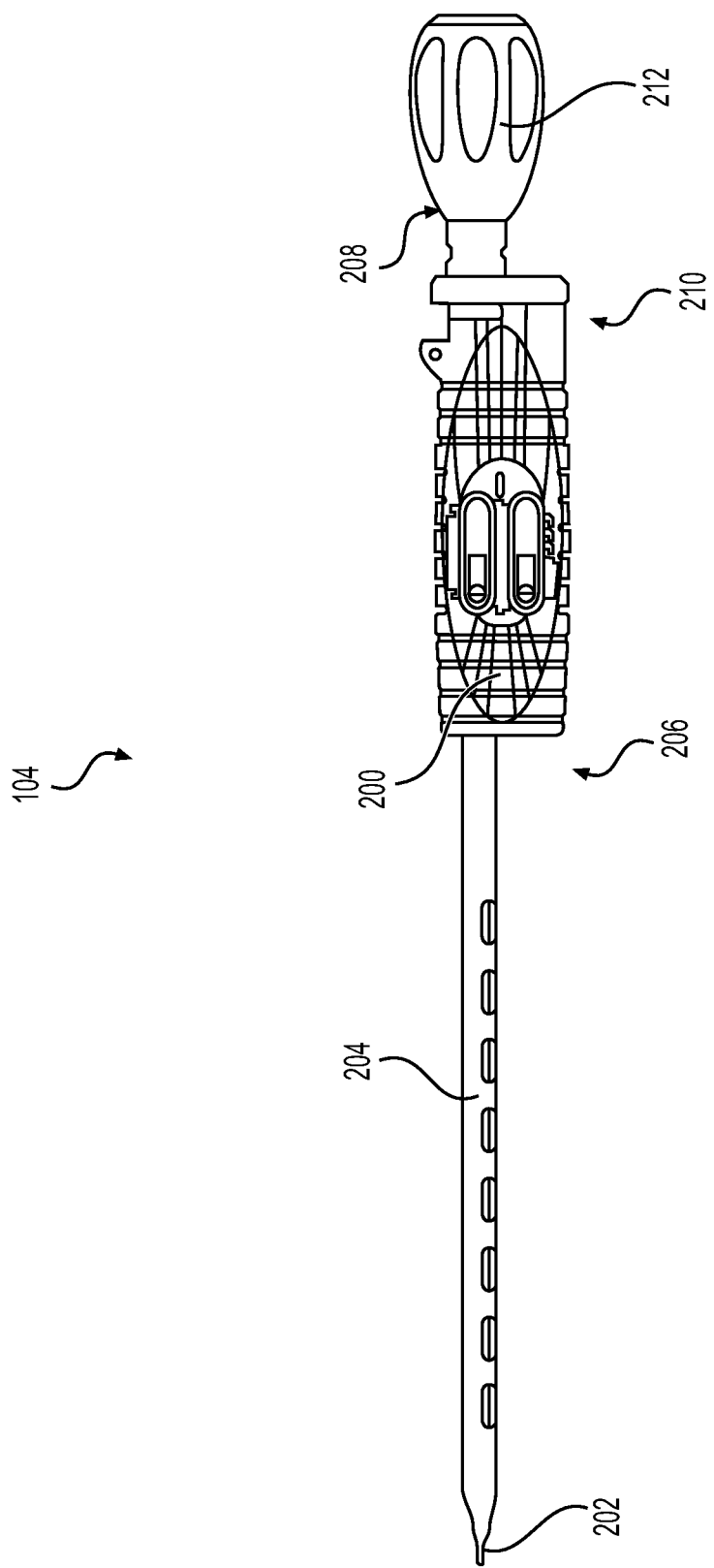
FIG. 2 is a side view of the surgical driver, according to some embodiments.

FIG. 2 illustrates a side view of the surgical driver 104, according to some embodiments. The surgical driver 104 includes a housing 200 with an inner driver shaft 202 and an outer driver shaft 204 extending out of a first side 206 of the housing 200. The surgical driver 104 further includes a driver key 208 configured to engage a second side 210 of the housing 200. In the illustrated embodiment, the second side 210 of the housing 200 is disposed opposite the first side 206 of the housing 200. However, the driver key 208 may be configured to engage any portion of the housing 200. As illustrated, the driver key 208 includes a handle 212. Rotating the handle 212 can cause rotation of the inner driver shaft 202, the outer driver shaft 204, or some combination thereof, which may cause the implant 102 of FIG. 1 to actuate (e.g., expand or collapse) when engaged with the surgical driver 104.

Figure 3:
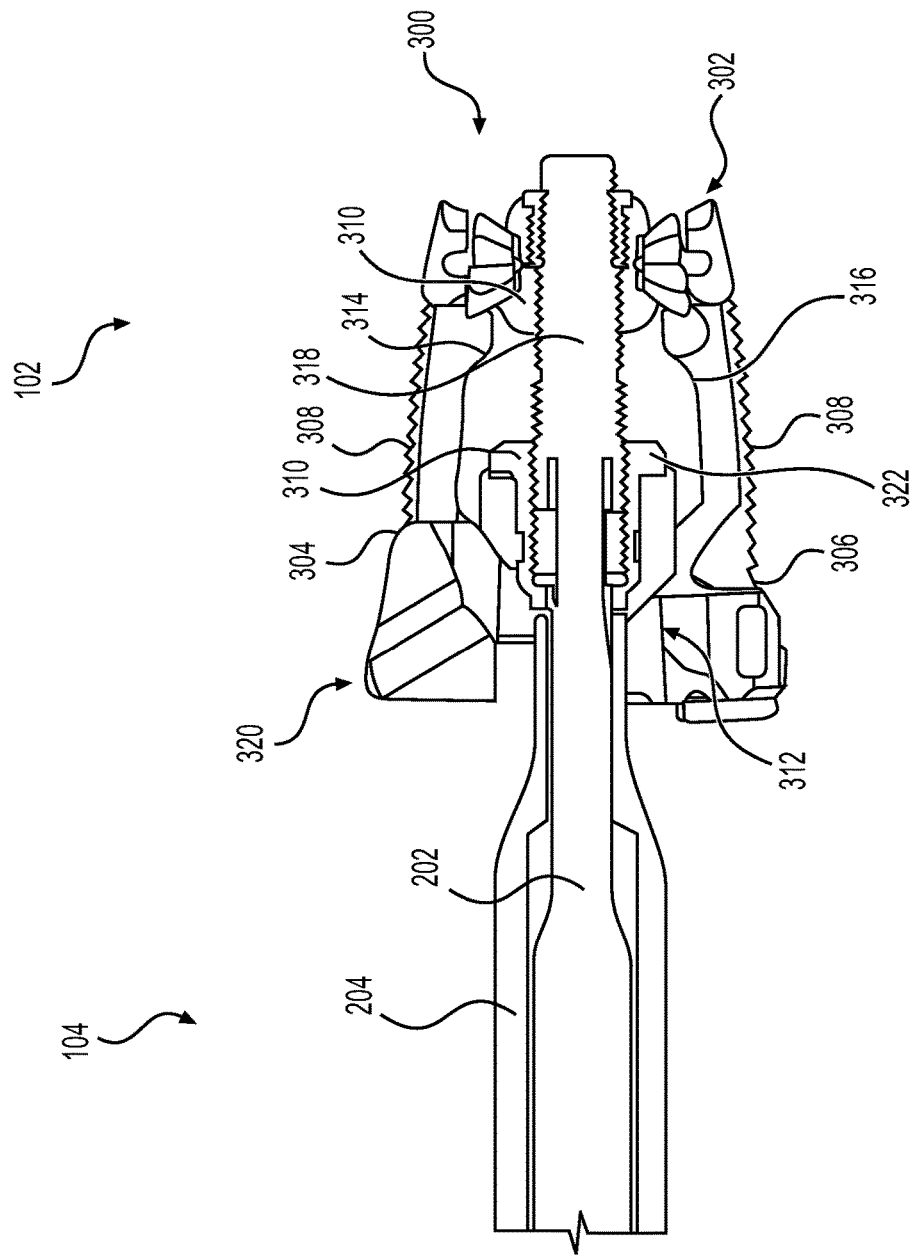
FIG. 3 is a cross-sectional view of the surgical driver engaged with the implant, according to some embodiments.

FIG. 3 is a cross-sectional view of the surgical driver 104 engaged with the implant 102, according to some embodiments. The implant 102 includes an upper endplate 300 and a lower endplate 302. Respective outer surfaces 304, 306 of the upper and lower endplates 300, 302 may have teeth 308 or other projections for penetrating body tissue to reduce a likelihood of migration of implant 102 after insertion. After insertion, the upper endplate 300 and the lower endplate 302 are configured to move with respect to each other to expand the implant 102 to a desired configuration, which may cause the teeth 308 or other projections to penetrate the body tissue and secure the implant 102. As illustrated, the endplates 300, 302 may be moveably coupled via a frame 312 secured to respective inner surfaces 314, 316 of the upper endplate 300 and the lower endplate 302. A plurality of moveable actuators 310, coupled to the frame 312 and positioned between the upper endplate 300 and the lower endplate 302, may be configured to move the endplates 300, 302. The implant 102 further includes an actuator screw 318 that extends through the plurality of moveable actuators 310 from an anterior end 320 of the implant 102. In other embodiments, multiple actuator screws may be contemplated. These multiple actuator screws may be designed to be parallel or coaxial with respect to each other.

Rotation of the actuator screw 318 with respect to the plurality of moveable actuators 310 causes at least one of the plurality of moveable actuators 310 to move with respect to the actuator screw 318, thereby causing the implant 102 to expand or collapse. As illustrated, the inner driver shaft 202 and the outer driver shaft 204 of the surgical driver 104 are configured to engage the implant 102. Specifically, the inner driver shaft 202 may be configured to engage the actuator screw 318 such that rotation of the inner driver shaft 202 may drive rotation of the actuator screw 318. Further, the outer driver shaft 204 may be configured to engage an anterior actuator 322 of the plurality of moveable actuators 310 such that rotation of the outer driver shaft 204 may drive rotation of the anterior actuator 322. The anterior actuator 322 may be disposed proximate an anterior end 320 of the implant 102. Relative motion between the plurality of moveable actuators 310 and the actuator screw 318 caused by rotation of the inner driver shaft 202, the outer driver shaft 204, or some combination thereof, causes the implant 102 to expand or collapse.

Figure 4:
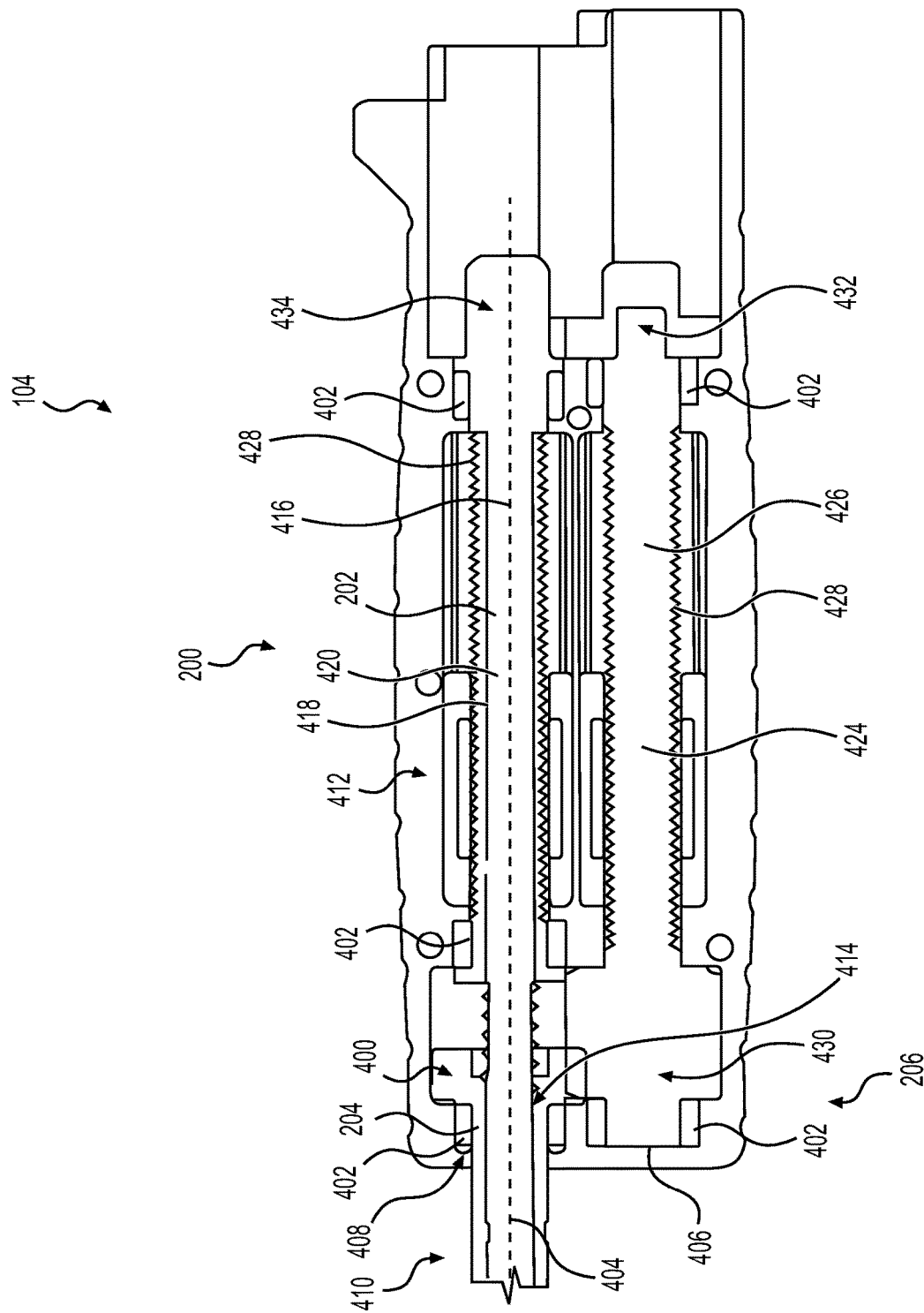
FIG. 4 is a cross-sectional view of a housing of the surgical driver, according to some embodiments.

In the illustrated embodiment, the inner driver shaft 202 and the outer driver shaft 204 are coaxial. As illustrated, the outer driver shaft 204 may be positioned around the inner driver shaft 202. The driver shafts 202, 204 may be configured to rotate independently from each other. Having coaxial driver shafts 202, 204 may allow for the inner and the outer driver shafts 202, 204 to engage and drive the implant 102 to expand or collapse through interaction with only the actuator screw 318 and anterior actuator 322. Thus, the coaxial driver shafts 202, 204 may provide for less invasive engagements with the implant 102 during a surgical operation than other drivers having multiple, neon-coaxial driver shafts 202, 204, FIG. 4 is a cross-sectional view of the housing 200 of the surgical driver 104, according to some embodiments. As illustrated, a proximal end 400 of the outer driver shaft 204 may be secured within the housing 200 of the surgical driver 104. One or more bearings 402 disposed within the housing 200 may at least partially secure the outer driver shaft 204. That is, the one or more bearings 402 may constrain the outer driver shaft 204 such that the outer driver shaft 204 may only move axially (e.g., along a central axis 404 of the outer driver shaft 204) and/or rotationally (e.g., with respect to the central axis of the outer driver shaft 204). The one or more bearings 402 may be secured to an interior of the housing 200. However, in some embodiments, the one or more bearings 402 are configured to sit within corresponding pockets 406 in the housing 200 configured to restrain movement of the one or more bearings 402. The one or more bearings 402 may be a plain bearing, a ball bearing, a roller bearing, or any suitable type of bearing for constraining radial motion, while permitting rotation, of the outer driver shaft 204. In some embodiments, the one or more bearings 402 may be formed in the housing 200. For example, a borehole 408 through the first side 206 of the housing 200 may form a bearing of the one or more bearings 402. The distal end 410 of the outer driver shaft 204 may be inserted through the one or more bearings 402 from an interior 412 of the housing 200 during assembly. Further, the proximal end 400 of the outer driver shaft 204 may have a greater diameter than a portion of the outer driver shaft 204 inserted through the at least one bearing. As such, the proximal end 400 of the outer driver shaft 204 may prevent axial movement of the outer driver shaft 204 through the first side 206 of the housing 200 during assembly and operation.

Moreover, the outer driver shaft 204 has a borehole 414 extending along the central axis 404 of the outer driver shaft 204. The inner driver shaft 202 may be configured to fit within the borehole 414 such that the outer driver shaft 204 and the inner driver shaft 202 are substantially coaxial during operation. The inner driver shaft 202 may be configured to rotate independently from the outer driver shaft 204. Further, the inner driver shaft 202 may be longer than the outer driver shaft 204. In the illustrated embodiment, the inner driver shaft 202 extends into the interior 412 of the housing 200 from the proximal end 400 of the outer driver shaft 204. The inner driver shaft 202 may extend through the one or more bearings 402 secured within the housing 200 such that the inner driver shaft 202 may be constrained to a desired orientation while still allowing rotation (e.g., with rotate with respect to the central axis 416 of the inner driver shaft 202) and axial movement (e.g., along the central axis 416 of the inner driver shaft 202) of the inner driver shaft 202.

The inner driver shaft 202 may include a threaded sleeve 418. In the illustrated embodiment, the threaded sleeve 418 may be secured to an exterior of a core shaft portion 420 of the inner driver shaft 202. In some embodiments, the threaded sleeve 418 includes a hole 422 extending along through the threaded sleeve 418. The hole 422 may have a non-circular cross-section such that rotation of the threaded sleeve 418 is dependent on rotation of the core shaft portion 420. For example, the hole 422 may have a hexagonal shaped cross section and a portion of the core shaft portion 420 may have a corresponding hexagonal shaped cross section such that the core shaft portion 420 may slide into the threaded sleeve 418. Further, as embodiments of the hole 422 are non-circular (e.g., hexagonal shaped), rotation of the core shaft portion 420 can rotate the threaded sleeve 418 (e.g., threaded portion). However, the hole 422 may have any suitable shaped cross-section (e.g., triangular, square, etc.). Alternatively, the threaded sleeve 418 may be integral to the inner driver shaft 202 such that the core shaft portion 420 may be threaded. That is, the core shaft portion 420 may be machined, or otherwise formed, to include threads 428.

As illustrated, an idler driver shaft 424 may also secured within the housing 200. Similar to the inner driver shaft 202, the idler driver shaft 424 may include a threaded sleeve 418 configured to rotate in response to rotation of a core idler driver shaft portion 426 of the idler driver shaft 424 or may include the threads 428 formed directly in the core idler driver shaft portion 426 of the idler driver shaft 424. Moreover, a distal end 430 of the idler driver shaft 424 may be positioned adjacent the first side 206 of the housing 200. The distal end 430 may be inserted into a bearing of the one or more bearings 402 secured to the first side 206 of the housing 200. A proximal end 432 of the idler driver shaft 424 may be positioned adjacent a second side 210 of the housing 200 such that the proximal end 432 of the idler driver shaft 424 may be positioned adjacent a proximal end 434 of the inner driver shaft 202. The idler driver shaft 424 may be radially offset from the inner driver shaft 202 and the outer driver shaft 204. Moreover, the idler driver shaft 424 may be mechanically connected to the outer driver shaft 204. That is, the idler driver shaft 424 may be connected to the outer driver shaft 204 such that rotation of the idler driver shaft 424 transmits torque to the outer driver shaft 204 as set forth in detail below.

Figure 5:
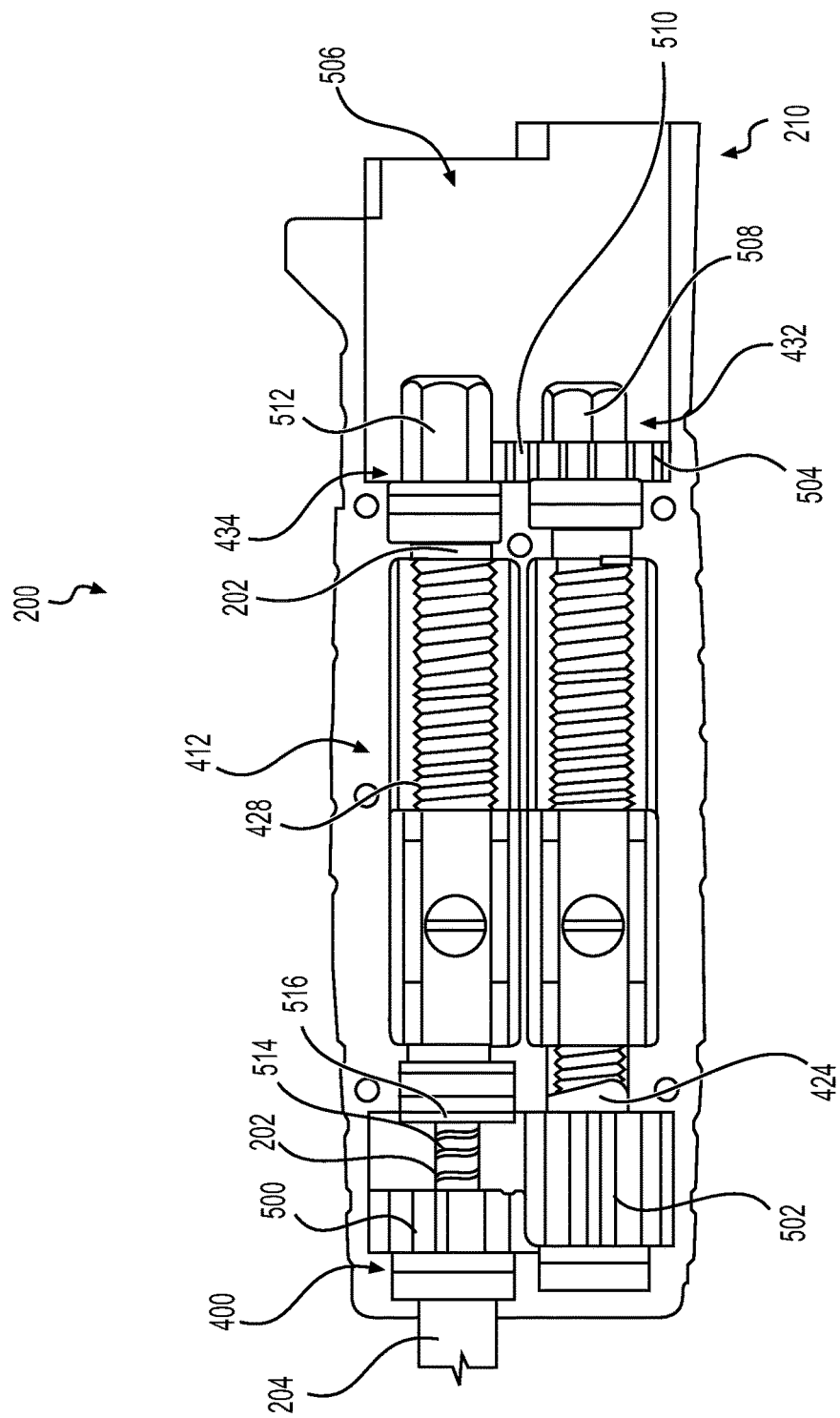
FIG. 5 is side view of an interior of the housing of the surgical driver, according to some embodiments.

FIG. 5 is a side view of the interior 412 of the housing 200 of the surgical driver 104, according to some embodiments. As set forth above, the idler driver shaft 424 may be mechanically connected to the outer driver shaft 204 such that rotation of the idler driver shaft 424 can transmit torque to the outer driver shaft 204. As illustrated, the outer driver shaft 204 includes an outer gear feature 500. The outer gear feature 500 may be formed at the proximal end 400 of the outer driver shaft 204 and disposed within the housing 200. Further, the idler driver shaft 424 includes a first idler gear feature 502 and a second idler gear feature 504. The outer gear feature 500 may be configured to mesh with a first idler gear feature 502. As such, rotation of the idler driver shaft 424 rotates the first idler gear feature 502, which transfer torque to the outer gear feature 500, and the torque transferred to the outer gear feature 500 rotates the outer driver shaft 204. Alternatively, inhibiting motion of the idler driver shaft 424 (e.g., counter-torqueing the idler driver shaft 424) may restrain rotation of the outer driver shaft 204.

Moreover, the housing 200 includes a keyhole 506. As illustrated, the keyhole 506 may be formed in the second side 210 of the housing 200. The proximal end 432 of the idler driver shaft 424 extends into the keyhole 506. In particular, the second idler gear feature 504 of the idler driver shaft 424 extends into the keyhole 506. Further, the idler driver shaft 424 includes an idler socket feature 508 extending into the keyhole 506 from the second idler gear feature 504 in a direction opposite the first side 206 of the housing 200 (e.g., toward the second side 210 of the housing 200). Thus, the idler socket feature 508 is may be at the proximal end 432 of the idler driver shaft 424 adjacent the second idler gear feature 504. The idler socket feature 508 may include a hexagonal shaped socket or any other suitably shaped socket feature. Further, the idler socket feature 508 may extend radially outward less than the second idler gear feature 504 such that the second idler gear feature 504 may be accessible from the keyhole 506. Indeed, the idler socket feature 508 may be sized such that gears 510 of the second idler gear feature 504 are accessible from the keyhole 506. Moreover, the idler socket feature 508 and the second idler gear feature 504 may be integral with the idler driver shaft 424. Alternatively, the idler socket feature 508 and the second idler gear feature 504 may be coupled and rotatably fixed to the idler driver shaft 424 such that rotating either the idler socket feature 508 or the second idler gear feature 504 rotates the idler driver shaft 424.

The proximal end 434 of the inner driver shaft 202 may also extend axially into the keyhole 506. The proximal end 434 of the inner driver shaft 202 may have an inner socket feature 512 extending into the keyhole 506. The inner socket feature 512 may include a hexagonal shaped socket or any other suitably shaped socket feature. In the illustrated embodiment, the inner socket feature 512 has a same size and shape as the idler socket feature 508, which may allow for a single corresponding socket to engage both the inner socket feature 512 and the idler socket feature 508. Further, the inner socket feature 512 may extend a same distance into the keyhole 506 as the idler socket feature 508. Moreover, the inner socket feature 512 may be integral with the inner driver shaft 202. Alternatively, the inner socket feature 512 may be coupled and rotatably fixed to the inner driver shaft 202 such that rotating the inner socket feature 512 rotates the inner driver shaft 202 independent of the outer driver shaft 204.

Moreover, the surgical driver 104 may include a spring 514 configured to bias the outer driver shaft 204. The spring 514 may be disposed around the inner driver shaft 202 between the proximal end 400 of the outer driver shaft 204 and the threads 428 of the inner driver shaft 202. In the illustrated embodiment, the spring 514 may be disposed between the proximal end 400 of the outer driver shaft 204 and an anchor feature 516 (e.g., a peek washer) secured to the interior of the housing 200. The spring 514 may be configured to bias the proximal end 400 of the outer driver shaft 204 toward the first end of the housing 200. During operation, the outer driver shaft 204 may engage the implant 102, e.g., as shown in FIG. 3. As the implant expands the anterior actuator 322 (e.g., shown in FIG. 3) engaged by the outer driver shaft 204 may retract into the implant 102 away from the outer driver shaft 204. To maintain contact between the outer driver shaft 204 and the anterior actuator 322, the outer driver shaft 204 may be configured to move toward the anterior actuator 322 under the biasing force from the spring 514. The outer driver shaft 204 may be configured to move axially with respect to the housing 200 and inner driver shaft 202. The spring 514 may transmit constant distal force to the outer driver shaft 204 as the inner and outer driver translate axially relative to one another.

Figure 6:
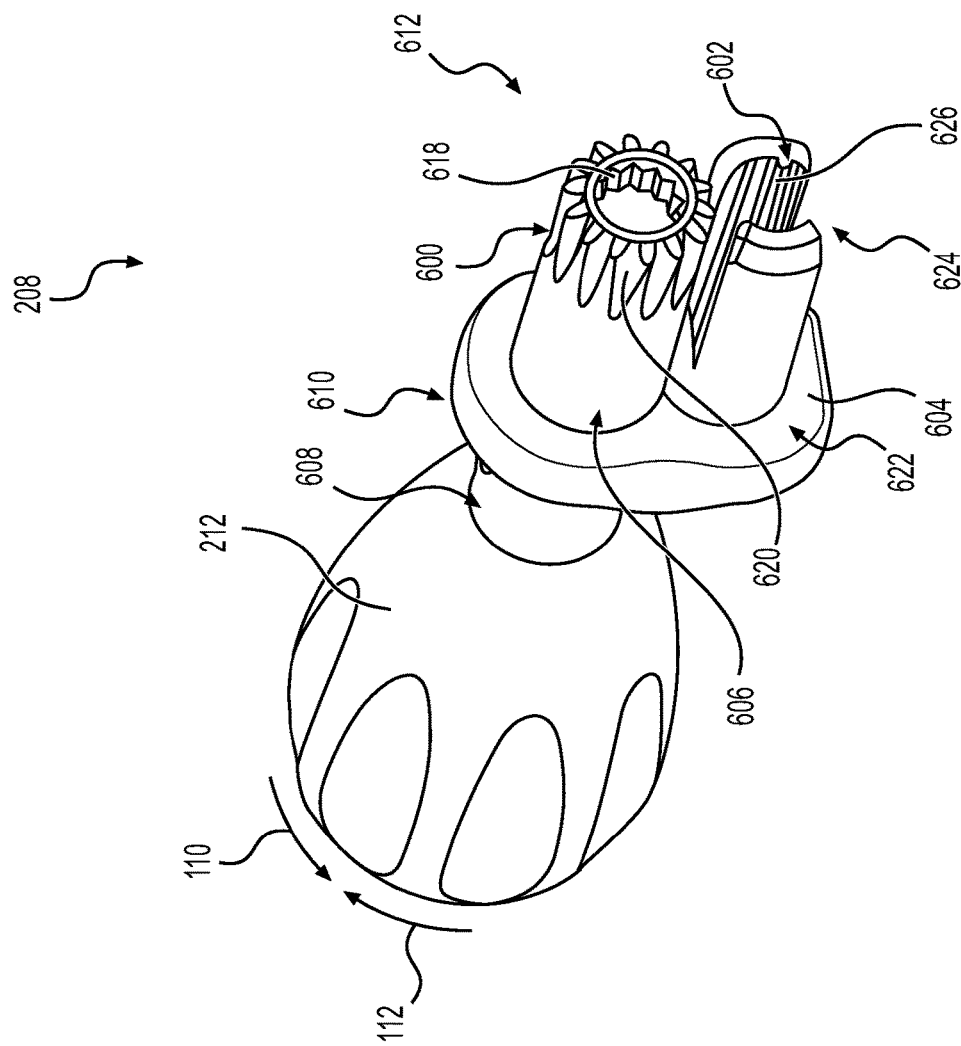
FIG. 6 is a perspective view of a driver key of the surgical driver, according to some embodiments.

FIG. 6 is a perspective view of a driver key 208 of the surgical driver 104, according to some embodiments. The driver key 208 may be configured to engage the keyhole 506 in the housing 200 shown in FIG. 5. The driver key 208 may engage the keyhole 506 in a first orientation, a second orientation, or a third orientation based on a desired configuration for the implant 102 of FIG. 3. As set forth in detail below, each orientation can be configured to cause the implant 102 to move into a unique configuration (e.g., the parallel expansion configuration, the anterior expansion configuration, and the posterior expansion configuration). The driver key 208 includes a driving feature 600, a counter-driving feature 602, the handle 212, and a body portion 604.

The driving feature 600 may be configured to rotate with respect to the body portion 604 of the driver key 208. The driving feature 600 may be substantially cylindrical and extend through a borehole 606 in the body portion 604 such that a proximal end 608 of the driving feature 600 may be positioned on a first side 610 of the body portion 604 and a distal end 612 of the driving feature 600 may be positioned on a second side 614 of the body portion 604. In some embodiments, the body portion 604 may include a bearing 616 at the borehole 606 to facilitate rotation of the driving feature 600 with respect to the body portion 604. Moreover, the handle 212 of the driving feature 600 may be coupled to the proximal end 608 of the driving feature 600. Rotating the handle 212 in the clockwise 110 direction may drive clockwise rotation of the driving feature 600 and rotating the handle 212 in the counterclockwise 112 direction may drive counterclockwise rotation of the handle 212. The distal end 612 of the driving feature 600 includes a first coupling mechanism 618 (e.g., an internal socket) and a second coupling mechanism 620 (e.g., an external gear feature). The first coupling mechanism 618 and the second coupling mechanism 620 may include any suitable coupling mechanisms for engaging the inner driver shaft 202 and the idler driver shaft 424 within the keyhole 506 (shown in FIG. 5). For example, the inner socket feature 512 of the inner driver shaft 202 may alternatively include an inner socket in one embodiment. Thus, the first coupling mechanism 618 may include a socket feature configured to engage the inner socket. However, in the illustrated embodiment, the first coupling mechanism 618 includes an internal socket, which may be sized for engaging the inner socket feature 512 and the idler socket feature 508. Further, the second coupling mechanism 620 includes the external gear feature, which may be sized to mesh with the second idler gear feature 504 while the internal socket may be engaged with the inner socket feature 512.

The counter-driving feature 602 may be fixed to the body portion 604 of the driver key 208 and extends outward from a second side 622 of the body portion 604 such that a distal end 624 of the counter-driving feature 602 may be positioned adjacent the distal end 612 of the driving feature 600. The counter-driving feature 602 may have a partial socket 626 sized to engage the inner socket feature 512 and idler socket feature 508 of the inner driver shaft 202 and the idler driver shaft 424, respectively. As the counter-driving feature 602 may be fixed to the body portion 604, the counter-driving feature 602 remains stationary with respect to the body portion 604 as the handle 212 rotates the driving feature 600. As such, the counter-driving feature 602 may be configured to impede rotation of any feature (e.g., the inner socket feature 512 or the idler socket feature 508 of FIG. 5) engaged with the counter-driving feature 602.

Figure 7:
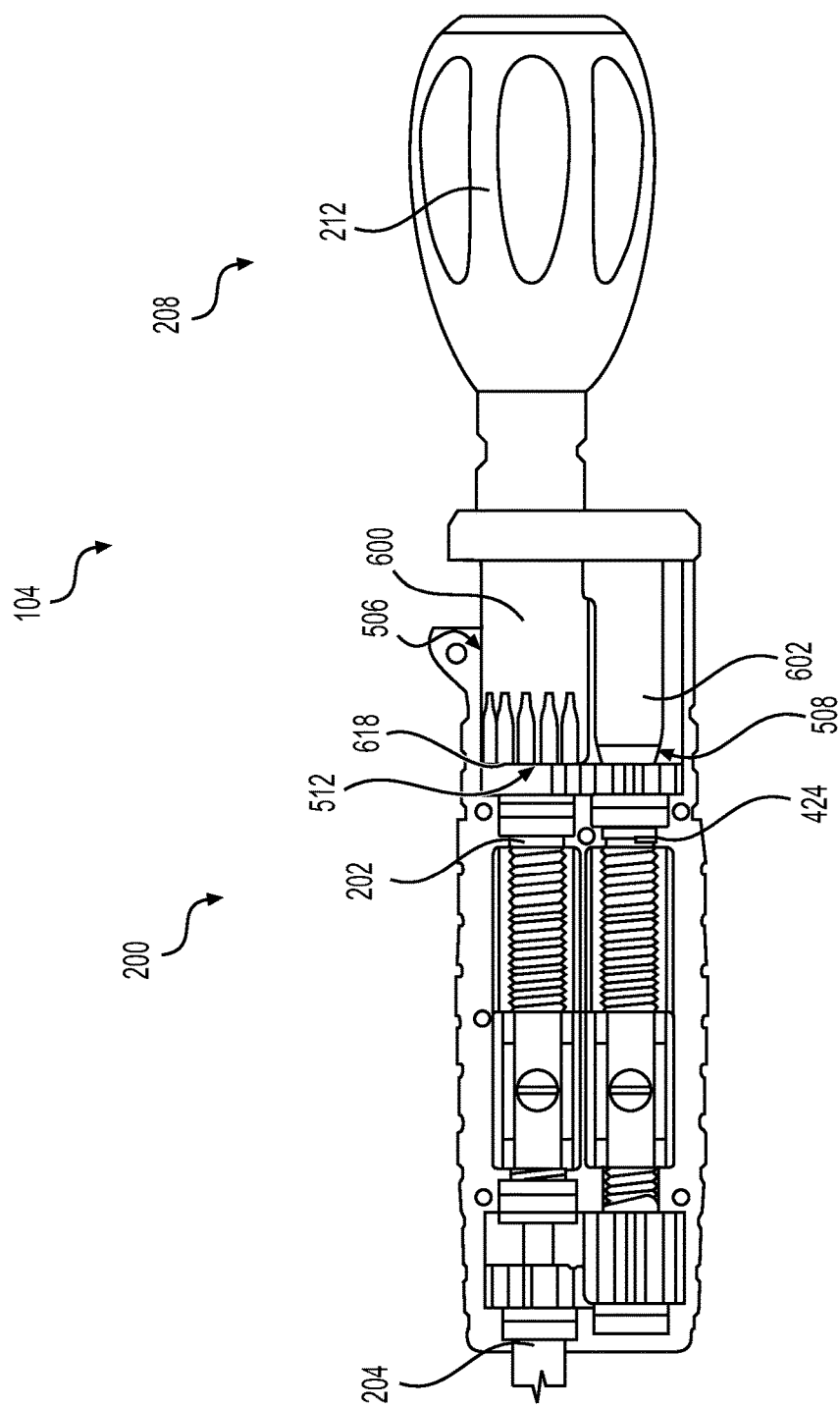
FIG. 7 is a cross-sectional view of the driver key engaging the housing of the surgical driver in a first orientation, according to some embodiments.

FIG. 7 illustrates a cross-sectional view of the driver key 208 engaging the housing 200 of the surgical driver 104 in a first orientation, according to some embodiments. Engaging the keyhole 506 of the housing 200 with the driver key 208 in the first orientation causes the implant 102 of FIG. 3 to expand toward the parallel expansion configuration in response to rotation of the surgical driver 104. In the first orientation, the driving feature 600 engages the inner driver shaft 202 such that rotation of the driving feature 600, via rotation of the handle 212, rotates the inner driver shaft 202. In the illustrated embodiment, the first coupling mechanism 618 (e.g., the internal socket) of the driving feature 600 may be configured to engage the inner socket feature 512 of the inner driver shaft 202 to drive rotation of the inner driver shaft 202.

Further, in the first orientation, the counter-driving feature 602 engages the idler driver shaft 424 to restrain rotation of the outer driver shaft 204. In particular, the counter-driving feature 602 may be configured to engage the idler socket feature 508 to restrain rotation of the idler driver shaft 424. As the idler driver shaft 424 may be mechanically connected to the outer driver shaft 204, restraining rotation of the idler driver shaft 424 also restrains rotation of the outer driver shaft 204. As set forth above, the inner driver shaft 202 may be disposed within the outer driver shaft 204 and may intermittently contact the outer driver shaft 204. As the inner driver shaft 202 rotates in the first orientation, frictional forces from contact between the inner driver shaft 202 and the outer driver shaft 204 may cause unwanted rotation of the outer driver shaft 204. However, the counter-driving feature 602 may restrain the outer driver shaft 204 in the first orientation to prevent the unwanted rotation. Further, as the inner driver shaft 202 and the outer driver shaft 204 are rotationally independent, the inner driver shaft 202 may still rotate when the counter-driving feature 602 restrains rotation of the outer driver shaft 204.

Figure 8:
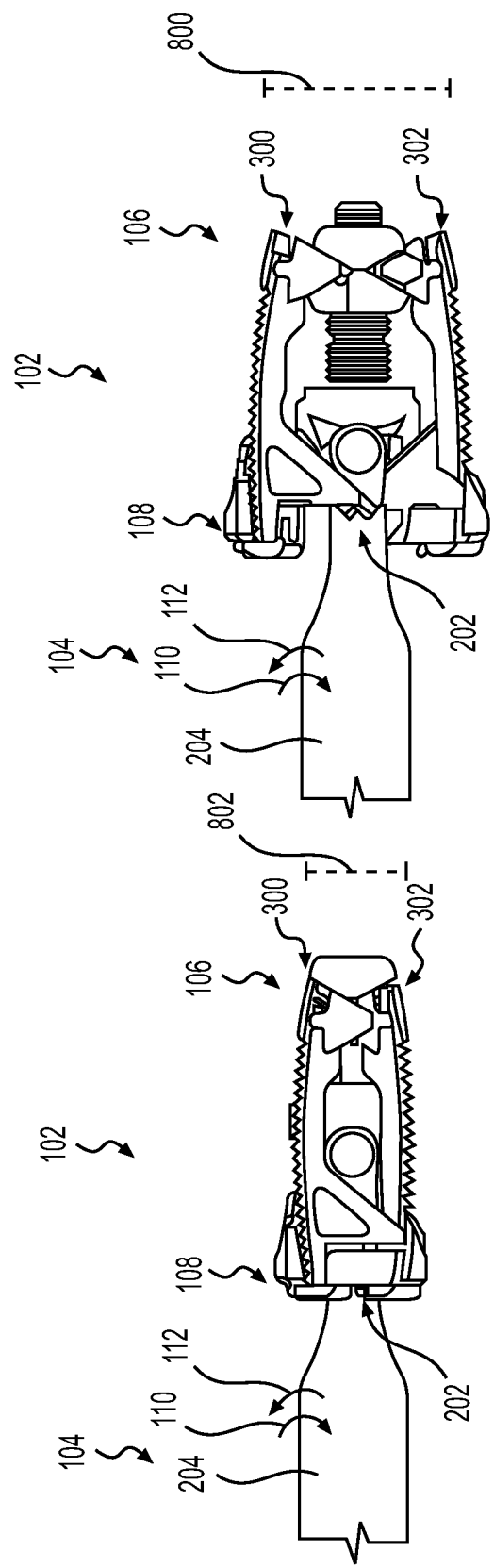
FIGS. 8A and 8B are side views of the implant in a collapsed configuration and a parallel expansion configuration, respectively, according to some embodiments.

FIGS. 8A and 8B are side views of the implant 102 in a collapsed configuration and a parallel expansion configuration, respectively, according to some embodiments. In the first orientation of the driver key 208 with respect to the housing 200 (shown in FIG. 7), the inner driver shaft 202 may be configured to rotate and the outer driver shaft 204 may be held in place. Specifically, in the first orientation, rotating the handle 212 of the surgical driver 104 (shown in FIG. 7) in a first direction (e.g., clockwise 110) causes clockwise rotation of the inner driver shaft 202. Clockwise rotation of the inner driver shaft 202, via clockwise rotation of the handle 212, may be configured to expand the endplates 300, 302 of the implant 102 in parallel toward the parallel expansion configuration, as shown in FIG. 8B. That is, rotating the inner driver shaft 202 may evenly expand posterior 106 and anterior portions 108 of the endplates 300, 302 of the implant 102. Rotating the inner driver shaft 202 in a second direction (e.g., counterclockwise 112) may collapse the implant 102 in parallel toward the collapsed configuration, as shown in FIG. 8A. The parallel expansion configuration may be maximum expansion of both the anterior portion 108 and the posterior portion 106 of the implant 102. In the parallel expansion configuration, the implant 102 may include a parallel expansion height 800 of XX inches for supporting adjacent vertebrae. However, in the first orientation, the endplates 300, 302 may be expanded in parallel to any height between a collapsed configuration height 802 and the parallel expansion height 800. For example, the implant 102 may be expanded to a height of XX inches via rotation of the surgical driver 104 in the first orientation.

Figure 9:
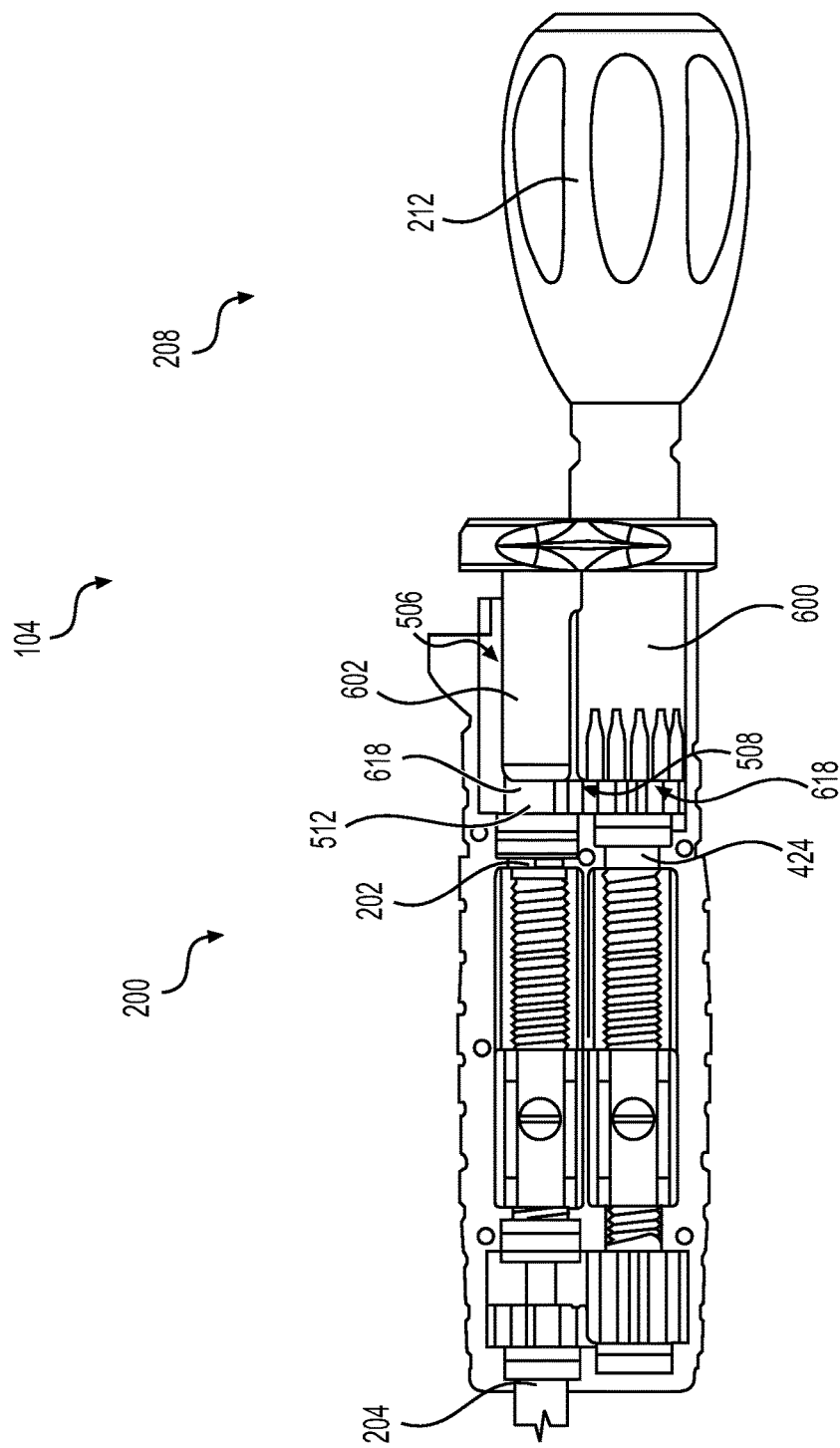
FIG. 9 is a cross-sectional view of the driver key engaging the housing of the surgical driver in a second orientation, according to some embodiments.

FIG. 9 is a cross-sectional view of the driver key 208 engaging the housing 200 of the surgical driver 104 in a second orientation, according to some embodiments. Engaging the keyhole 506 of the housing 200 with the driver key 208 in the second orientation causes the implant 102 of FIG. 3 to expand toward the anterior expansion configuration in response to rotation of the surgical driver 104. In the second orientation, the driving feature 600 engages the idler driver shaft 424 such that rotation of the driving feature 600, via rotation of the handle 212, rotates the idler driver shaft 424. In the illustrated embodiment, the first coupling mechanism 618 (e.g., the internal socket) of the driving feature 600 may be configured to engage the idler socket feature 508 of the idler driver shaft 424 to drive rotation of the idler driver shaft 424, which drives rotation of the outer driver shaft 204.

Further, in the second orientation, the counter-driving feature 602 engages the inner driver shaft 202 to restrain rotation of the inner driver shaft 202. In particular, the counter-driving feature 602 may be configured to engage the inner socket feature 512 to restrain rotation of the inner driver shaft 202. As set forth above, the inner driver shaft 202 may be disposed within the outer driver shaft 204 such that the outer driver shaft 204 may intermittently contact the inner driver shaft 202. As the outer driver shaft 204 rotates in the first orientation, frictional forces from contact between the outer driver shaft 204 and the inner driver shaft 202 may cause unwanted rotation of the inner driver shaft 202. However, the counter-driving feature 602 may restrain the inner driver shaft 202 in the second orientation to prevent the unwanted rotation. Further, as the outer driver shaft 204 and the inner driver shaft 202 are rotationally independent, the outer driver shaft 204 may still rotate when the counter-driving feature 602 restrains rotation of the inner driver shaft 202

FIGS. 10A and 10B are side views of the implant 102 in a collapsed configuration and an anterior expansion configuration, respectively, according to some embodiments. In the second orientation of the driver key 208 with respect to the housing 200 shown in FIG. 9, the outer driver shaft 204 may be configured to rotate and the inner driver shaft 202 may be held in place. Specifically, in the second orientation, rotating the handle 212 of FIG. 9 in a first direction (e.g., clockwise 110) causes counterclockwise rotation of the outer driver shaft 204. Counterclockwise rotation of the outer driver shaft 204, via clockwise rotation of the handle 212, may be configured to expand the implant 102 toward the anterior expansion configuration, as shown in FIG. 10B. That is, counterclockwise rotation of the outer driver shaft 204 may expand anterior portions 108 of the endplates 300, 302 of the implant 102. Rotating the handle 212 of the surgical driver 104 a second direction (e.g., counterclockwise 112) cause the outer driver shaft 204 to rotate in the clockwise direction to collapse the anterior portion the implant 102 toward the collapsed configuration, as shown in FIG. 10A. The anterior expansion configuration may be maximum expansion of the anterior portion 108 of the implant 102. In the anterior expansion configuration, the anterior portions 108 of the endplates 300, 302 of the implant 102 may be expanded to form a maximum lordotic angle 1000 for the implant 102. The maximum lordotic angle 1000 for the implant 102 may be thirty degrees. Alternatively, the maximum lordotic angle 1000 may be between twenty-five to thirty-five degrees, between fifteen to twenty-five degrees, or any other suitable range for the lordotic angle. However, in the second orientation, the anterior portions 108 of the endplates 300, 302 may be expanded to form any lordotic angle less than the maximum lordotic angle. For example, the implant 102 may be expanded to form a lordotic angle of 10 degrees via rotation of the surgical driver 104 in the second orientation.

Figure 11:
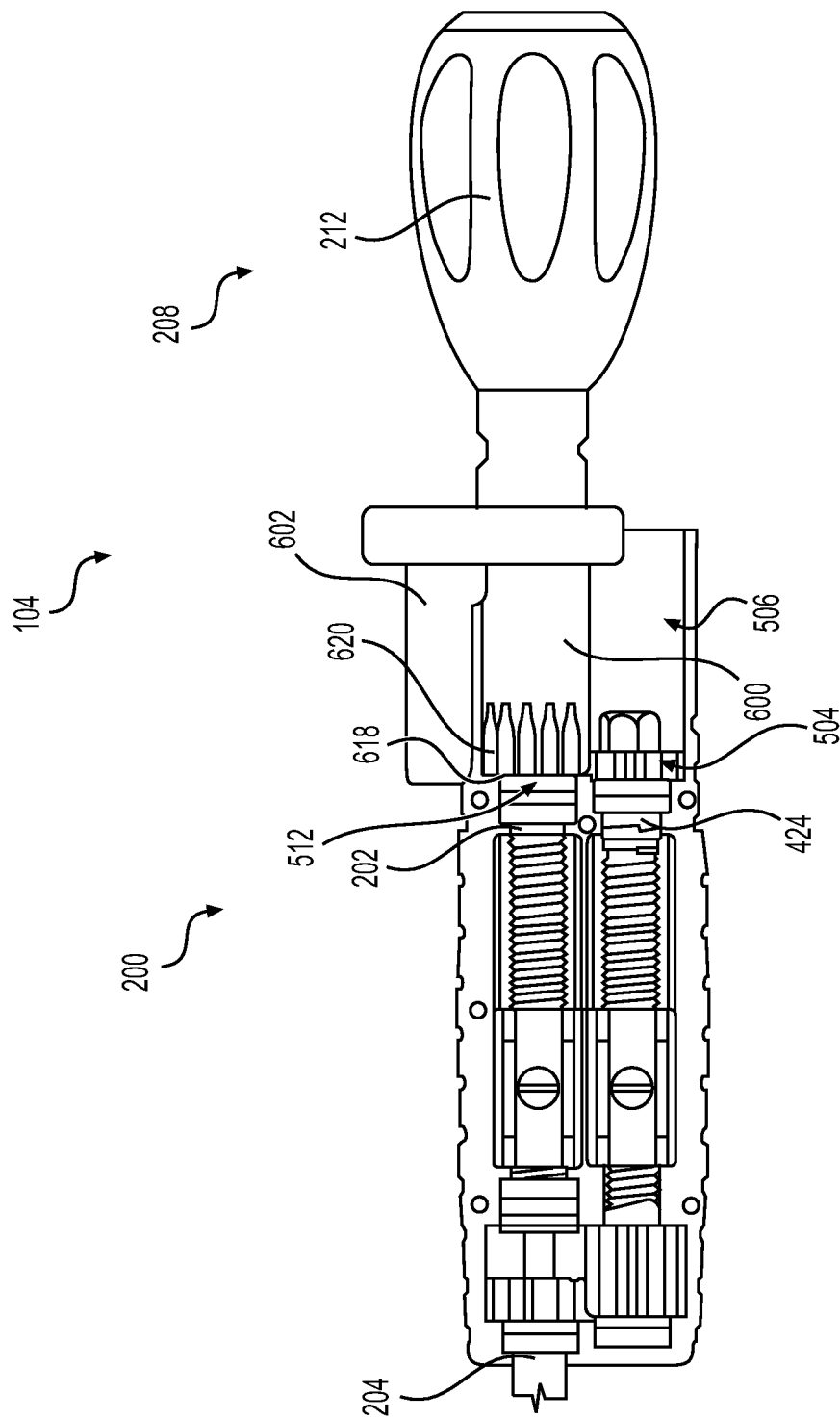
FIG. 11 is a cross-sectional view of the driver key engaging the housing of the surgical driver in a third orientation, according to some embodiments.

FIG. 11 is a cross-sectional view of the driver key 208 engaging the housing 200 of the surgical driver 104 in a third orientation, according to some embodiments. Engaging the keyhole 506 of the housing 200 with the driver key 208 in the third orientation causes the implant 102 of FIG. 3 to expand toward the posterior expansion configuration in response to rotation of the surgical driver 104. In the third orientation, the driving feature 600 engages both the inner driver shaft 202 and the idler driver shaft 424 such that rotation of the driving feature 600, via rotation of the handle 212, rotates the inner driver shaft 202 and the outer driver shaft 204. In the illustrated embodiment, the first coupling mechanism 618 (e.g., the internal socket) of the driving feature 600 may be configured to engage the inner socket feature 512 of the inner driver shaft 202 to drive rotation of the idler driver shaft 424. Further, the second coupling mechanism 620 (e.g., the external gear feature) may be configured to mesh with the second idler gear feature 504 of the idler driver shaft 424 to drive rotation of the idler driver shaft 424, which also causes the outer driver shaft 204 to rotate. Further, in the third orientation, the counter-driving feature 602 is not inserted into the keyhole 506. Instead, the counter-driving feature 602 may be disposed outside of the housing 200 such that the counter-driving feature 602 does not restrain rotation of either the inner driver shaft 202 or the idler driver shaft 424.

Figure 12A:
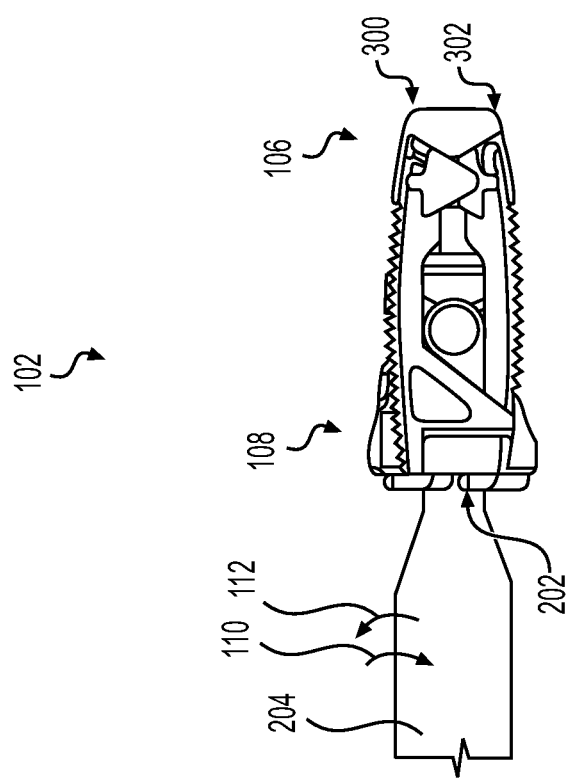
FIGS. 12A and 12B are side views of the implant in a collapsed configuration and a posterior expansion configuration, respectively, according to some embodiments.
Figure 12B:
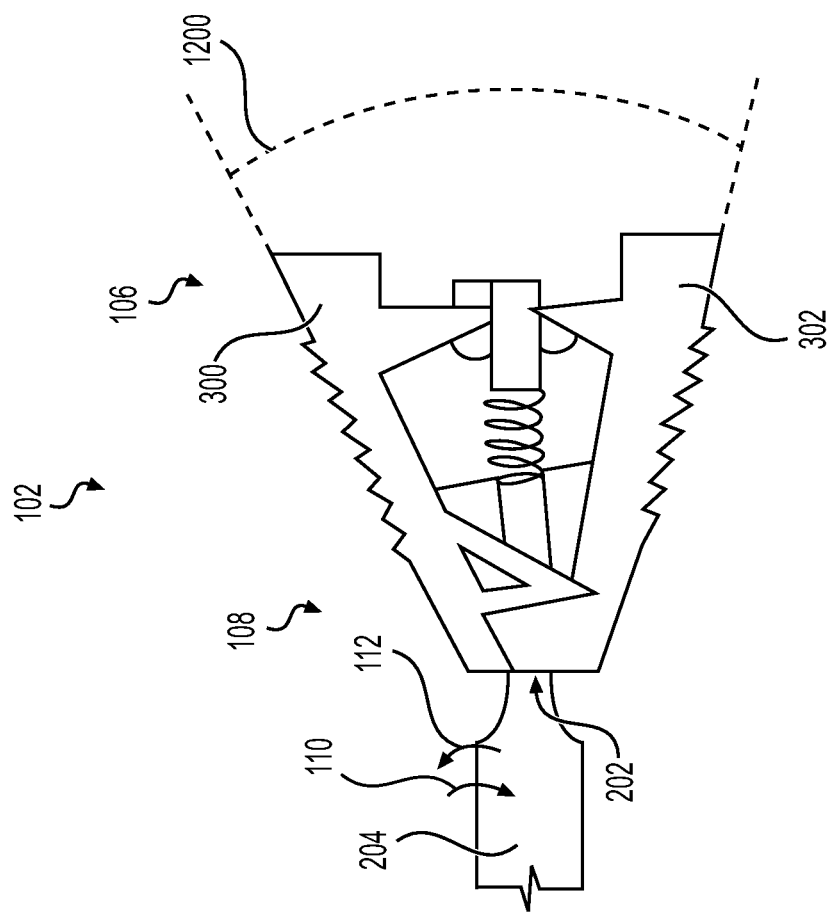

FIGS. 12A and 12B are side views of the implant 102 in a collapsed configuration and a posterior expansion configuration, respectively, according to some embodiments. In the third orientation of the driver key 208 with respect to the housing 200 of FIG. 11, both the outer driver shaft 204 and the inner driver shaft 202 are configured to rotate. Specifically, in the third orientation, rotating the handle 212 of FIG. 11 in a first direction (e.g., clockwise 110) causes clockwise rotation of the inner driver shaft 202 and counterclockwise rotation of the outer driver shaft 204. Clockwise rotation of the inner driver shaft 202 and counterclockwise rotation of the outer driver shaft 204, via clockwise rotation of the handle 212, may be configured to expand the implant 102 toward the posterior expansion configuration, as shown in FIG. 12B. That is, clockwise rotation the inner driver shaft 202 and counterclockwise rotation of the outer driver shaft 204 may expand posterior portions 106 of the endplates 300, 302 of the implant 102.

Rotating the handle 212 of the surgical driver 104 in a second direction (e.g., counterclockwise 112) may reverse rotational directions of the inner driver shaft 202 and the outer driver shaft 204 to collapse the anterior portions 108 of the endplates 300, 302 of the implant 102 toward the collapsed configuration, as shown in FIG. 12A. The posterior expansion configuration may be maximum expansion of the posterior portion 106 of the implant 102. In the posterior expansion configuration, the posterior portions 106 of the endplates 300, 302 of the implant 102 may be expanded to form a maximum posterior lordotic angle 1200 for the implant 102. The maximum posterior lordotic angle 1200 for the implant 102 may be thirty degrees. Alternatively, the maximum posterior lordotic angle may be between twenty-five to thirty-five degrees, between fifteen to twenty-five degrees, or any other suitable range for the posterior lordotic angle. However, in the third orientation, the posterior portions 106 of the endplates 300, 302 may be expanded to form any posterior lordotic angle less than the maximum posterior lordotic angle 1200. For example, the implant 102 may be expanded to form a posterior lordotic angle of 10 degrees via rotation of the surgical driver 104 in the third orientation.

Moreover, the implant 102 may be expanded via multiple orientations of the driver key 208. For example, the implant 102 may require that the anterior portion 108 of the implant 102 have a first expansion height of and the posterior portion 106 of the implant 102 have a larger second expansion height. In some embodiment, the implant 102 may be expanded in parallel via the first orientation until both the anterior portion 108 and the posterior portion 106 of the implant 102 are expanded to the first expansion height. Then the driver key 208 may be removed and reoriented to the third orientation. In the third orientation, rotation of the surgical driver 104 may continue to expand the posterior portion 106 of the implant 102 to the second expansion height while maintaining the anterior portion 108 of the implant 102 at the first expansion height. Accordingly, various configurations of implant 102 may be achieved.

Figure 13:
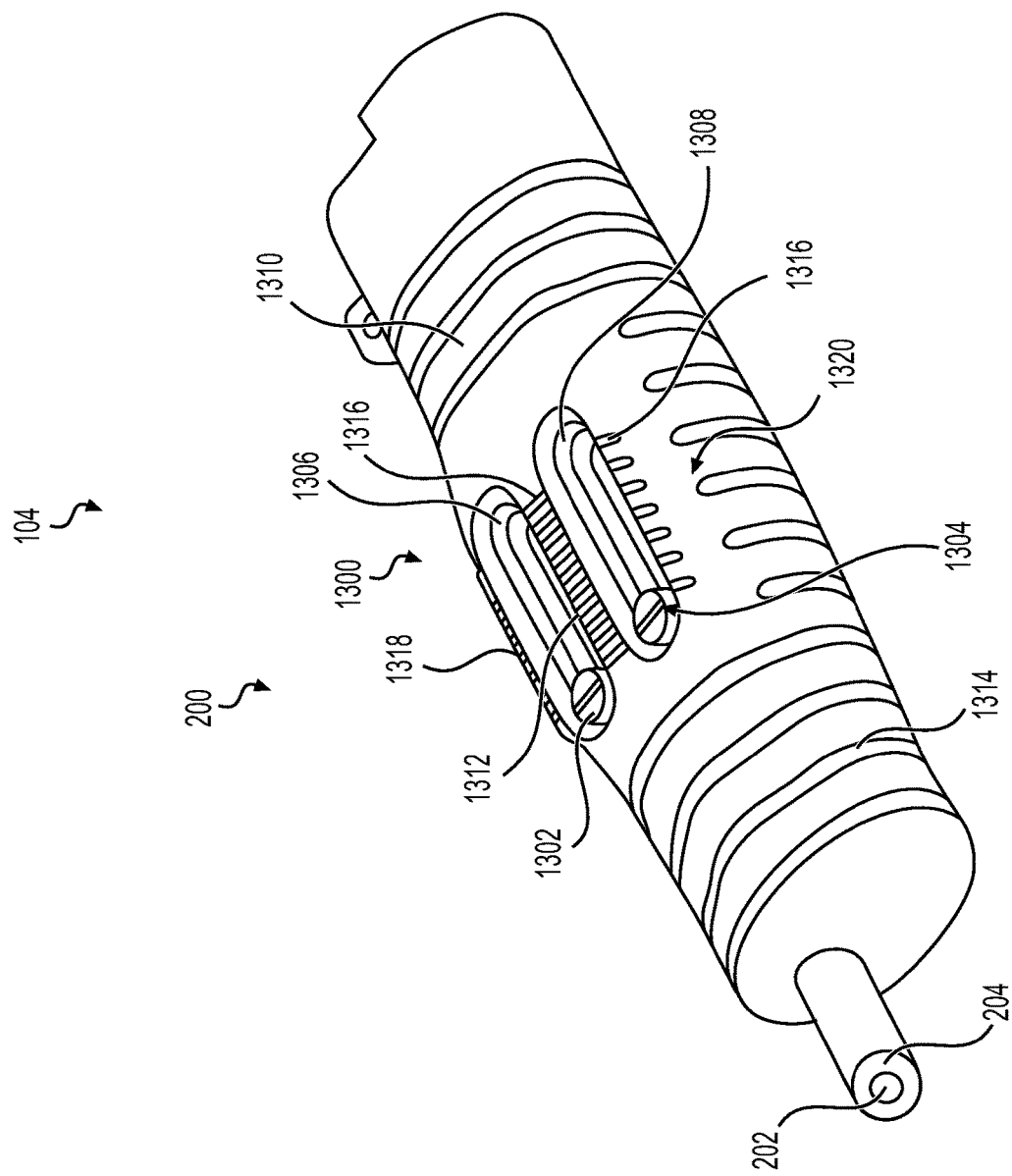
FIG. 13 is a perspective view of the housing of the surgical driver having a measurement device, according to some embodiments.

FIG. 13 is a perspective view of the housing 200 of the surgical driver 104 having a measurement system 1300, according to some embodiments. As set forth above, the housing 200 of the surgical driver 104 remains stationary relative to the movement of the inner driver shaft 202 and the outer driver shaft 204. As the housing 200 is relatively stationary, the housing 200 provides a stable reference frame for counting driver revolutions to take expansion measurements, which may be advantageous during a surgical operation. The measurement values are based on rotation of the inner and outer driver shafts 202, 204, as rotation of the driver shafts 202, 204 may be related to expansion of the implant 102 of FIG. 3. Rotation of the inner and outer driver shafts 202,204 may be determined based on axial movement of the respective driver shafts 202, 204. Respective button dials (e.g., a first button dial 1302 and a second button dial 1304) may be coupled to corresponding driver shafts 202, 204 such that axial movement of the driver shafts 202, 204 may be observed via movement of the respective buttons 1302, 1304 along corresponding slots (e.g., a first slot 1306 and a second slot 1308) extending through a face 1310 of the housing 200. Thus, as the movement of the respective button dials 1302, 1304 relates to movement of the respective driver shafts 202, 204, movement of the respective driver shafts 202, 204 relate to rotation of the driver shafts 202, 204, and rotation of the driver shafts 202, 204 relate to expansion of the implant 102, measurement values for the implant 102 may be determined via movement of the respective button dials 1302, 1304.

Figure 14:
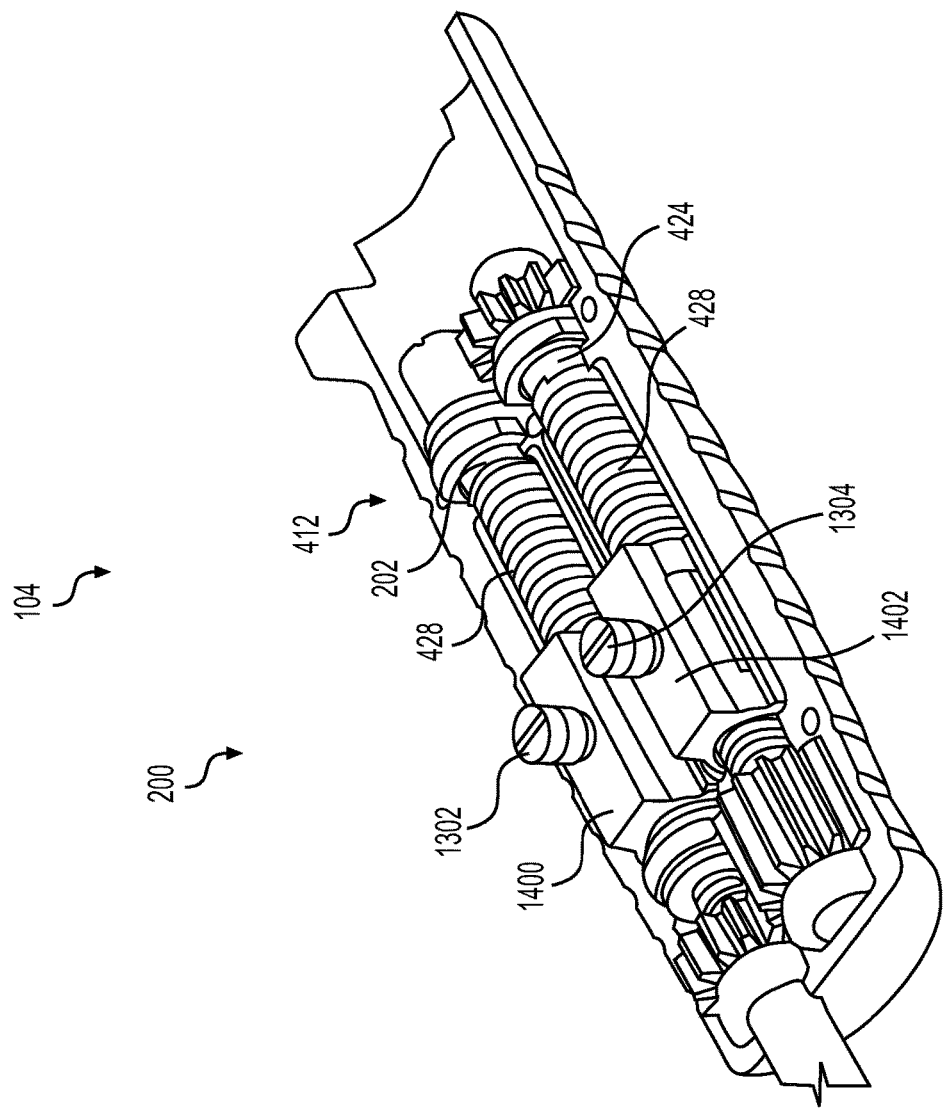
FIG. 14 is a perspective view of the interior of the housing of the surgical driver having the measurement device, according to some embodiments.

As illustrated, the housing 200 has measurement scales 1312 on an exterior portion 1314 of the housing 200. The measurement scales 1312 may be positioned proximate the first slot 1306 and the second slot 1308. Measurements of the implant height (e.g., posterior expansion height and anterior expansion height) and the lordotic angle may be determined based on positions of the button dials 1301, 1304 relative to the measurement scales 1312. As illustrated, the measurement scales 1312 include markings 1316 corresponding to various values for a posterior expansion height, anterior expansion, height, and/or lordosis angle of the implant 102 of FIG. 3. In particular, posterior expansion height measurements of the implant may be determined using a position of the first but dial 1302 relative to a top scale 1318 of the measurement scales 1312. Further, the lordotic angle may be determined based on a positioned of the second button dial 1304 with respect to a bottom scale 1320 of the measurement scales 1312, Moreover, anterior expansion height may be calculated based on a posterior expansion measurement and the lordosis angle, FIG. 14 is a perspective view of the interior 412 of the housing 200 of the surgical driver 104 having the measurement device, according to some embodiments. The respective button dials (e.g., the first button dial 1302 and the second button dial 13043 may be coupled to the corresponding driver shafts (e.g., the inner driver shaft 202 and the idler driver shaft 424) via an inner shaft thread follower 1400 and an idler shaft thread follower 1402. The thread followers 1400, 1402 are configured to move axially with the respective driver shafts 202, 204 as the respective driver shafts 202, 204 rotate such that the movement of the respective button dials 1302, 1304 relate to movement of the respective driver shafts 202, 204. Moreover, each thread follower 1400, 1402 may be secured to respective threads of the inner driver shaft 202 and the idler driver shaft 424.

Figure 15:
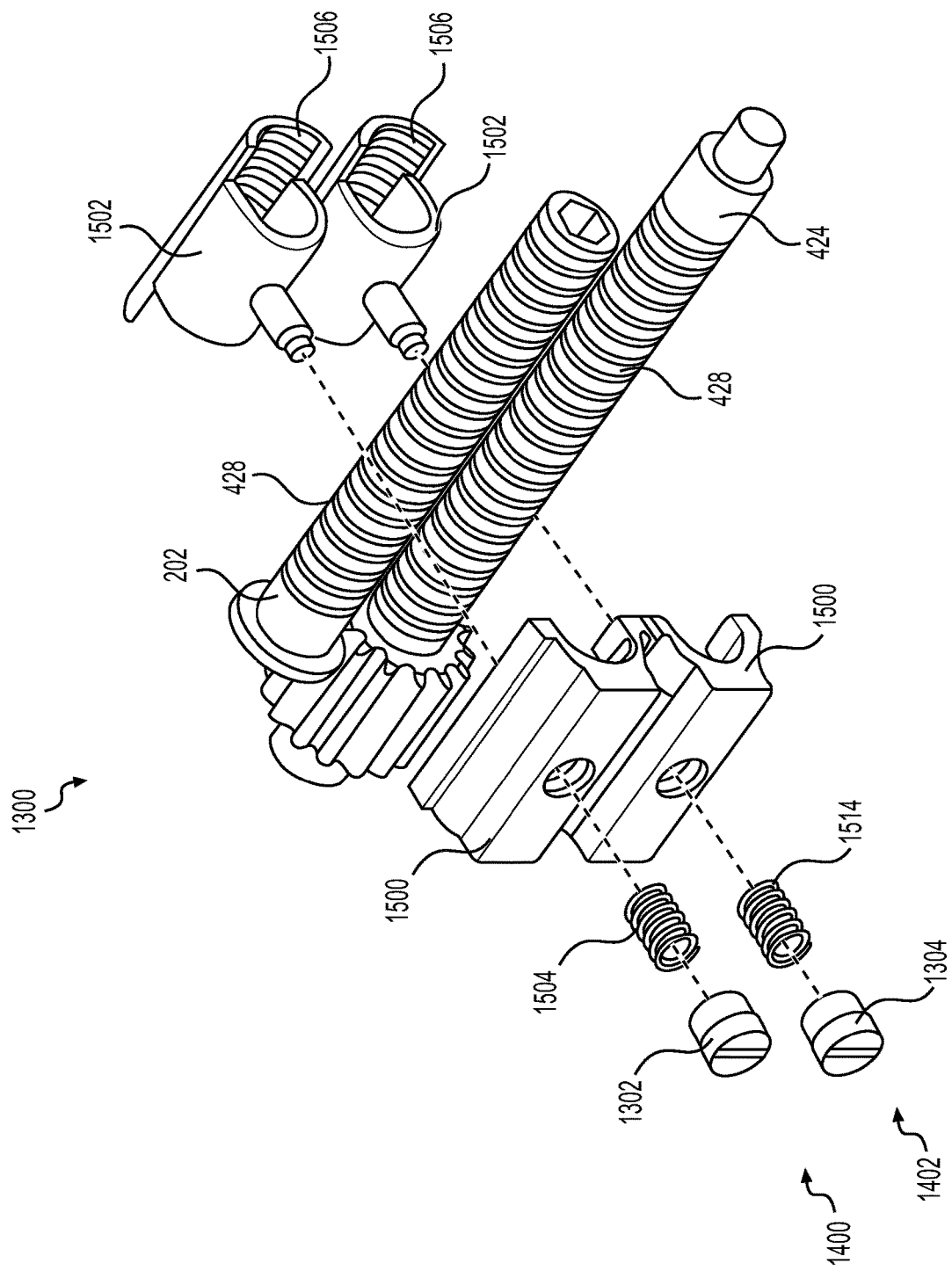
FIG. 15 is an exploded view of the measurement device, according to some embodiments.

FIG. 15 is an exploded view of the measurement system, according to some embodiments. As set forth above, the measurement system 1300 includes the inner shaft thread follower 1400 and the idler shaft thread follower 1402. Each of the thread followers 1400, 1402 may include a slider 1500, a threaded carriage 1502, a compression spring 1504, and the respective button dial 1302, 1304. The respective button dial 1302, 1304 may be coupled to the slider 1500 and/or the compression spring 1504, The slider 1500 may be coupled to the threaded carriage 1502 and configured to move axially along the first slot 1306 or the second slot 1308 (shown in FIG. 13) as the respective driver shaft (e.g., inner driver shaft 202 or idler driver shaft. 4241 moves with respect to the housing 200. Moreover, the threaded carriage 1502 has internal threads 1506 configured to mesh with the respective threads 428 of the inner driver shaft 202 and the idler driver shaft 424. The threaded carriages 1404 may secure the thread followers 1400, 1402 to the respective driver shafts 202, 204.

FIGS. 16A and 16B are cross-sectional views of the thread follower 1400 of the measurement system 1300 in an engaged state and a disengage state, respectively, according to some embodiments. As set forth above, each of the thread follower 1400 may include the slider 1500, the threaded carriage 1502, the compression spring 1504, and the first button dial 1302. The compression spring 1504 may be configured to bias the threaded carriage 1502 to engage with the inner driver shaft 202, as shown in FIG. 16A. However, actuating the first, button dial 1302 may disengage the threaded carriage 1502 from the threads 428 of the inner driver shaft 202, as shown in FIG. 16B. That is, force on the first button dial 1302 moving the first button dial 1302 toward the slider 1500 may compress the compression spring 1504 and move the threaded carriage 1502 laterally away from the central axis 416 of the inner driver shaft 202, thereby, allowing the thread follower 1400 to be freely translated within its limits of travel, which may provide for quick calibration or resetting of the measurement system 1300.

In other embodiments, multiple surgical drivers may be used to provide various expansion function. For example, in one embodiment, a first driver may be used to expand a posterior portion of the implant and a second driver may be used to expand an anterior portion of the implant. It is also contemplated that the surgical driver shafts may be configured to dock with the implant. For example, the driver shafts may be threadedly docked to the implant. Other docket mechanisms such as a dovetail, or a keyed mating feature may also be used to dock the driver shafts to the implant.

In the above description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. An implant expansion driver for expanding an intervertebral implant, comprising:
   a housing;
   a first driver shaft disposed in the housing and extending distally therefrom, the first driver shaft configured to rotate with respect to the housing and configured to couple to an actuation screw of the implant;
   a second driver shaft disposed in the housing and extending distally therefrom, wherein the second driver shaft is an outer shaft coaxially positioned around the first driver shaft, configured to rotate with respect to the housing and configured to couple to an actuator of the implant, the first and second driver shafts being configured to rotate independently to selectively expand a proximal end or a distal end of the implant;
   an idler driver shaft disposed in the housing;
   a gear coupling the idler driver shaft to the second driver shaft; and
   a driver key configured to removably attach to the housing in first and second orientations relative to the housing to selectively rotate the first and second driver shafts so as to expand both the proximal and distal ends of the implant together or expand one of the proximal and distal ends of the implant relative to the other end, and wherein the driver key is configured to selectively lock or unlock the second driver shaft based on the orientation of the driver key.

2. The implant expansion driver of claim 1, wherein the driver key includes a handle, and wherein rotation of the handle:
   in a first circumferential direction expands the implant regardless of the orientation of the driver key relative to the housing; and
   in a second circumferential direction opposite the first circumferential direction contracts the implant regardless of the orientation of the driver key.

3. The implant expansion driver of claim 2, wherein the driver key is configured to removably attach to the housing in a third orientation relative to the housing to rotate the first and second driver shafts together.

4. The implant expansion driver of claim 3, wherein when the driver key in the third orientation rotates the first and second driver shafts together, the actuation screw and the actuator rotate together to expand the distal end of the implant.

5. The implant expansion driver of claim 1, wherein the driver key includes a driving feature, a counter-driving feature, and a handle, and wherein rotation of the handle:
   in a first circumferential direction expands the implant regardless of the orientation of the driver key relative to the housing; and
   in a second circumferential direction opposite the first circumferential direction contracts the implant regardless of the orientation of the driver key.

6. The implant expansion driver of claim 1, wherein the driver key is configured to removably attach to the housing in a third orientation relative to the housing to rotate the first and second driver shafts together.

7. The implant expansion driver of claim 6, wherein when the driver key in the third orientation rotates the first and second driver shafts together, the actuation screw and the actuator rotate together to expand the distal end of the implant.

8. A surgical implant system, comprising:
   an intervertebral implant including:
   an upper endplate;
   a lower endplate;
   a frame;

a plurality of moveable actuators received in the frame and positioned between the upper endplate and the lower endplate; and an actuation screw that extends through the plurality of moveable actuators, wherein rotation of the plurality of moveable actuators and the actuation screw causes the implant to expand in parallel or unevenly between the proximal end and the distal end; and an implant expansion driver including:

a housing;

a first driver shaft disposed in the housing and extending distally therefrom, the first driver shaft configured to rotate with respect to the housing and configured to couple to the actuation screw of the implant;

a second driver shaft disposed in the housing and extending distally therefrom, wherein the second driver shaft is an outer shaft coaxially positioned around the first driver shaft, configured to rotate with respect to the housing and configured to couple to at least one of the plurality of moveable actuators of the implant, the first and second driver shafts being configured to rotate independently to selectively expand the proximal end and the distal end of the implant;

an idler driver shaft disposed in the housing;

a gear coupling the idler driver shaft to the second driver shaft; and a driver key configured to removably attach to the housing in first and second orientations relative to the housing to selectively rotate the first and second driver shafts so as to expand both the proximal end and the distal end of the implant together or expand one of the proximal end and the distal end of the implant relative to the other end, and wherein the driver key is configured to selectively lock or unlock the second driver shaft based on the orientation of the driver key.

9. The surgical implant system of claim 8, wherein the driver key includes a handle, and wherein rotation of the handle: in a first circumferential direction expands the implant regardless of the orientation of the driver key relative to the housing; and in a second circumferential direction opposite the first circumferential direction contracts the implant regardless of the orientation of the driver key.

10. The surgical implant system of claim 9, wherein the driver key is configured to removably attach to the housing in a third orientation relative to the housing to rotate the first and second driver shafts together.

11. The surgical implant system of claim 10, wherein when the driver key in the third orientation rotates the first and second driver shafts together, the actuation screw and the at least one of plurality of moveable actuators rotate together to expand the distal end of the implant.

12. The surgical implant system of claim 8, wherein the driver key includes a driving feature, a counter-driving feature, and a handle, and wherein rotation of the handle: in a first circumferential direction expands the implant regardless of the orientation of the driver key relative to the housing; and in a second circumferential direction opposite the first circumferential direction contracts the implant regardless of the orientation of the driver key.

13. The surgical implant system of claim 8, wherein the driver key is configured to removably attach to the housing in a third orientation relative to the housing to rotate the first and second driver shafts together.

* * * * *